United States Patent [19]

Alexander

[11] Patent Number: 5,030,218
[45] Date of Patent: Jul. 9, 1991

[54] COMPOSITION OF BLADE OF ELECTROSURGICAL INSTRUMENT

[76] Inventor: Lee Alexander, 8609 Piper La., Largo, Fla. 34647

[21] Appl. No.: 426,727

[22] Filed: Oct. 26, 1989

Related U.S. Application Data

[63] Continuation of Ser. No. 301,383, Jan. 25, 1989, abandoned.

[51] Int. Cl.⁵ .............................................. A61B 17/35
[52] U.S. Cl. ....................................... 606/45; 606/49; 128/783
[58] Field of Search ....................... 606/39, 40, 41, 44, 606/45, 49; 128/783, 784

[56] References Cited

U.S. PATENT DOCUMENTS

| | | | |
|---|---|---|---|
| 2,110,735 | 10/1933 | Marton | 606/44 |
| 3,595,239 | 7/1971 | Petersen | 606/45 |
| 3,920,022 | 11/1975 | Pastor | 606/41 |
| 4,440,178 | 4/1984 | Bussard et al. | 128/784 |
| 4,678,546 | 7/1987 | Yu-Zhang | 204/37.6 |

OTHER PUBLICATIONS

A New Dictionary of Chemistry, M. Miall, 1940 1st. Publ., p. 373.

Primary Examiner—Max Hindenburg
Assistant Examiner—Robin R. Longo
Attorney, Agent, or Firm—Beveridge, DeGrandi & Weilacher

[57] ABSTRACT

An electrosurgical blade to which eschar is less adherent, and which therefore requires less interruption during the operation for cleaning of the blade. The blade is of niobium covered by coating of niobium oxide.

1 Claim, 1 Drawing Sheet

COMPOSITION OF BLADE OF ELECTROSURGICAL INSTRUMENT

CROSS-REFERENCE TO RELATED APPLICATION

This invention is disclosed in part in my co-pending application entitled ELECTROSURGICAL INSTRUMENT, Ser. No. 07/301,383, abandonded, filed on Jan. 25, 1989, which this application is a continuation.

BACKGROUND OF THE INVENTION

1. Field of the Invention

This invention relates to electrosurgical instruments capable of selectively cutting tissue and coagulating blood.

In all surgical procedures, and particularly cardiac or major vascular procedures, hemostasis or the control of bleeding is of the utmost importance. Electrocautery is the principal method used in surgery to achieve hemostasis.

The electrosurgical device consists of three components. In the first component, high frequency electrical energy is generated in an Electrical Surgical Unit, often called a "Bovie" after one of the earliest brands.

The second component is the instrument held by the surgeon, and is often called a pencil. It contains an electrical switch, and is connected to the electrical surgical unit by a cord. The pencil also holds the blade.

During the operation, the blade, with a low charge, is touched to the bleeding vessel and the surrounding tissue and coagulation occurs. The protein, also called eschar, coagulates on the blade.

The blade, at a high charge, is also used for cutting. In this mode, the electric curent actually vaporizes the adjacent tissue, which serves to bake the buildup onto the blade.

Over the course of the operation this buildup interfers with the electrical qualities of the blade and the surgeon must interrupt the operation to scrape the blade on an abrasive surface. When sufficient damage has been done to the blade, a new blade must be substituted.

2. Description of the Prior Art

The conventional balde for an electrosurgical instrument today is made of stainless steel. A recognized problem with these blades is that blood and tissue, or eschar, tend to adhere to and carbonize on the blade. This requires the suregon to interrupt the procedure at frequent intervals to clean the blade.

U.S. Pat. No. 4,228,800, entitled Bipolar Electrosurgical Knife, inventor Howard F. Degler, Jr. et. al. discloses bipolar electrosurgical blade with a center electrode. The criteria for the structure for the center electrode is said to be stringent than those for the side electrodes. The center electrode must be both reasonably refractory and medically acceptable. The preferred metals are stainless steel or tantalum.

U.S. Pat. No. 3,768,482, entitled Surgical Cutting Instrument Having Electrically Heated Cutting Edge, inventor Robert F. Shaw discloses an electrosurgical blade of tantalum nitride or other metal with a positive temperature coefficient of resistance. The stated object is to maintain a constant high temperature, generally between 300–1,000 C.

U.S. Pat. No. 4,682,596, entitled Electrosurgical Catheter and Method For Vascular Applications, inventor Thomas O. Bales discloses a method and device for removing atheroscleric placque buildup in blood vessels. One version discloses a catheter with a stainless steel tip which is a monopolar electrode. The tip may alternatively be platinum or tantalum. This tip may include an ultra thin insulating layer, such as ceramic metal oxide for capacitively coupling electrical energy to tissue.

U.S. Pat. No. 4,333,467, entitled Nonstick Conductive Coating, inventor Joseph J. Domincone discloses a non-stick coating comprising a first layer of conductive material deposited on the substrate and covered by a layer of organic non-stick material such as silicone.

U.S. Pat. No. 4,719,914, entitled Electrosurgical Instrument, inventor Gerald W. Johnson discloses an instrument with an attached moveable vacuum hood. The purpose of the moveable hood is to remove the eschar buildup during the operation.

U.S. Pat. No. 4,563,691 entitled Electrosurgical Electrode, inventor Judy Lindstron, discloses a electrosurgical hooked blade of stainless steel covered by telfon for athroscopy.

U.S. Pat. No. 4,785,807, entitled Electrosurgical Knife, inventor G. Marsden Blanch discloses a stainless steel blade, covered with a primer, and then covered by teflon.

U.S. Pat. No. 4,440,178 entitled Implantable Electrode, inventor Adrien Bussard discloses a cardiac pacemaker electrode. The electrode body is a sintered metal covered with a coating having a higher electrical resistance. A variety of metals are mentioned as suitable including niobium.

SUMMARY OF THE INVENTION

An electrosurgical blade to which eschar is less adherent, and which therefore requires less interruption during the operation for cleaning of the blade. The blade is of niobium covered by coating of niobium oxide.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, and the scopes of the invention will be indicated in the claims.

BRIEF DESCRIPTION OF THE DRAWINGS

The invention will be better understood and the objects other than those set forth above will become apparent when consideration is given to the following detailed description thereof. Such description makes reference to the annexed drawings wherein.

DESCRIPTION OF THE PREFERRED EMBODIMENTS

The conventional electrosurgical instrument comprises a disposable handle, often called a pencil, into which a blade is inserted. Instead of a blade, a needle, ball, loop or wire may be used. The instrument is powered by a high frequency power source, typically at 400 KH and 400 volts.

The blade of the present invention is made of niobium onto which is deposited a surface coating of niobium oxide. To produce this coating, the electrode is anodized in a bath of 0.1% phosphoric acid, at a temperature of 90° C., and 40 ma per sq. in. for ten minutes. As is known the depth of niobium oxide can be varied by altering the voltage of the anodization treatment and the density varies with time.

Figure 2:
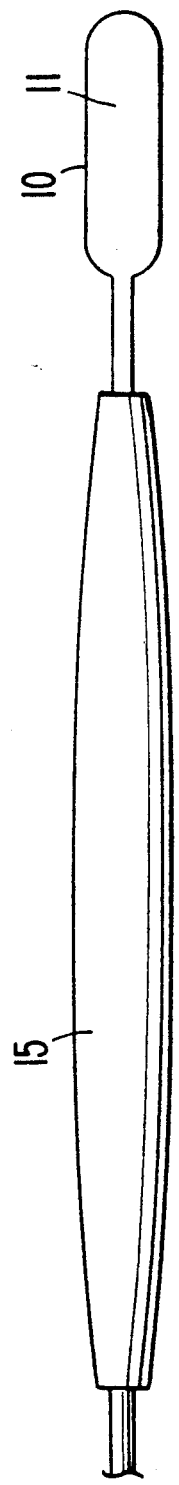
FIG. 2 is a side view of the pencil and the blade.

FIG. 2 shows the blade (10) attached to the pencil (15).

Figure 1:
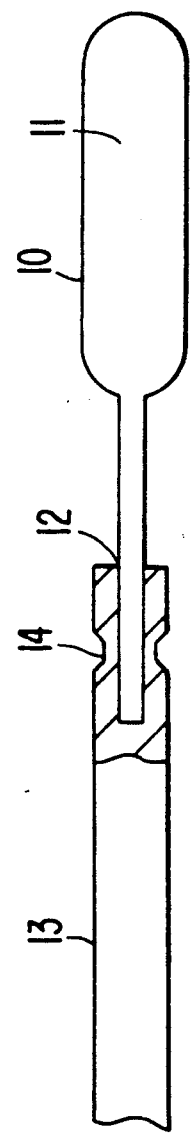
FIG. 1 is a cross sectional view of the blade of the present invention.

FIG. 1 illustrates a niobium blade (10) onto which has been deposited a covering of niobium oxide (11). The distal end (12) of the blade fits into an axial aperture of a stainless steel rod (13). The forward end (14) of the rod is crimped or swaged onto the distal end (12) of the blade (10). This composite structure of the electrode reduces the cost of the electrode by reducing the amount of expensive metal.

In use this blade is more stick resistant to a build up of blood and tissue, or eschar, than the conventional blades of stainless steel. This reduces the amount of time of the operation and the time the patient is subjected to the effects of anesthesia. This blade of niobium covered by niobium oxide is more stick resistant than a blade of stainless steel. The blade has better conductivity and lasts much longer than the conventional blade of stainless steel.

We have also made a blade of tantalum covered by tantalum oxide which exhibits the same stick resistant properties a niobium covered by niobium oxide. We expect similar properties from any biocompatible refractory metals, which include molybdenum tungsten and titanium, or alloys of refractory metals.

Further research has revealed that a blade of pure niobium gives similar stick free characteristics as the composite blade. Polishing the blade improves the stick free characterisitics, but is not necessary.

We have also found out that a composite blade may be made which gives these characterisitcs. The body or shaft may be stainless steel, brass or other metal. The blade may be pure niobium, niobium covered with niobium oxide, pure tantalum covered with a tantalum oxide, pure titanium covered with a titanium oxide, or stainless steel covered with platinum. The distal end of the shaft is fitted into an insulator and connected to a wire carrying the electric current.

The blades as described above last during most entire procedures as compared with stainless steel. They offer better conductivity and easier cut, i.e. less drag or resistance through tissue.

The use of such materials treated in this way is not limited to electrosurgical instrument blades, but may be quite useful in a considerable variety of other surgical instruments, such as bipolar forceps and argon beam instruments.

It will thus be seen that the objects set forth above, among those made apparent from the preceding description, are efficiently attained and, since certain changes may be made in carrying out the above method and in the article set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An electrosugical instrument for use with a source of radio frequency electrical energy comprising in combination:
   (a) a handle having an aperture into which a portion of a blade is inserted and through which electrical energy is passed;
   (b) a blade;
   (c) said blade having a first section comprising a stainless steel shaft fitting into the aperture of said handle;
   (d) said stainless steel shaft having an axial aperture at the end opposite the end fitting into said handle;
   (e) said blade having a second section of a second metal, one end of which is elongated and flattened, the other end of which is circular and fits within the axial aperture of said stainless steel section;
   (f) said second section of the blade being covered with niobium oxide,
whereby the niobium-niobium oxide blade provides a more stick resistent surface for electrosurgery.

* * * * *